US007623251B2

(12) United States Patent
Neal et al.

(10) Patent No.: US 7,623,251 B2
(45) Date of Patent: Nov. 24, 2009

(54) GEOMETRIC MEASUREMENT SYSTEM AND METHOD OF MEASURING A GEOMETRIC CHARACTERISTIC OF AN OBJECT

(75) Inventors: Daniel R. Neal, Tijeras, NM (US); Thomas Daniel Raymond, Edgewood, NM (US); William Shea Powers, Albuquerque, NM (US)

(73) Assignee: AMO Wavefront Sciences, LLC., Albuquerque, NM (US)

( * ) Notice: Subject to any disclaimer, the term of this patent is extended or adjusted under 35 U.S.C. 154(b) by 394 days.

(21) Appl. No.: 11/783,315

(22) Filed: Apr. 9, 2007

(65) Prior Publication Data

US 2007/0236702 A1    Oct. 11, 2007

Related U.S. Application Data

(60) Provisional application No. 60/789,901, filed on Apr. 7, 2006.

(51) Int. Cl.
*G01B 11/14* (2006.01)
(52) U.S. Cl. ..................................... 356/625
(58) Field of Classification Search .......... 356/625–630
See application file for complete search history.

(56) References Cited

U.S. PATENT DOCUMENTS

| 4,707,137 A | 11/1987 | Lee |
| 5,333,049 A | 7/1994 | Ledger |
| 5,416,586 A | 5/1995 | Tronolone et al. |
| 5,526,336 A | 6/1996 | Park et al. |
| 5,563,709 A | 10/1996 | Poultney |
| 5,629,765 A | 5/1997 | Schmutz |
| 5,641,437 A | 6/1997 | Williams et al. |
| 5,684,762 A | 11/1997 | Kubo |
| 5,847,827 A | 12/1998 | Fercher |
| 5,960,379 A | 9/1999 | Shimizu et al. |
| 6,184,974 B1 | 2/2001 | Neal et al. |
| 6,624,894 B2 | 9/2003 | Olszak et al. |
| 6,624,896 B1 | 9/2003 | Neal et al. |
| 6,741,335 B2 | 5/2004 | Kinrot et al. |
| 6,909,498 B2 | 6/2005 | Devie et al. |
| 6,956,657 B2 | 10/2005 | Golini et al. |
| 6,972,850 B2 | 12/2005 | Ohtsuka et al. |
| 7,009,696 B2 | 3/2006 | Sullivan et al. |
| 7,289,213 B2 | 10/2007 | Mieher et al. |
| 7,455,407 B2 * | 11/2008 | Neal et al. .................. 351/221 |
| 2005/0174568 A1 | 8/2005 | Vaez-Iravani et al. |
| 2007/0002334 A1 | 1/2007 | Altman et al. |
| 2007/0177156 A1 | 8/2007 | Mansfield |

FOREIGN PATENT DOCUMENTS

EP    1204893    12/2002

* cited by examiner

*Primary Examiner*—Michael P Stafira (57) ABSTRACT

A geometric measurement system is adapted to precisely measure one or more surfaces of objects such as corneas, molds, contact lenses in molds, contact lenses, or other objects in a fixture. The geometric measurement system can employ one or more of three possible methods of measurement: Shack-Hartmann wavefront sensing with wavefront stitching; phase diversity sensing; and white light interferometry.

18 Claims, 8 Drawing Sheets

GEOMETRIC MEASUREMENT SYSTEM AND METHOD OF MEASURING A GEOMETRIC CHARACTERISTIC OF AN OBJECT

CROSS-REFERENCES TO RELATED APPLICATIONS

This patent application claims the priority benefit under 35 U.S.C. §119(e) from U.S. provisional patent application 60/789,901 filed on 7 Apr. 2006 in the names of Daniel Neal et al., the entirety of which is hereby incorporated herein by reference for all purposes as if fully set forth herein.

BACKGROUND AND SUMMARY

1. Field

This invention pertains to the field of measurements, and more particularly, to a geometric measurement system and a method of making geometric measurements of an object using light reflected and/or refracted from one or more surfaces of the object.

2. Description

There are many examples of measurement or metrology systems that are designed to measure or characterize an object's surface. Among these systems are optically-based systems which operate by reflecting or scattering light from the object's surface and then collecting and analyzing the reflected or scattered light. These systems may use any of a number of principles such as, but not limited to, interferometry, Moiré deflectometry, heterodyne interferometry, laser triangulation, phase diversity wavefront sensing, or Shack-Hartmann (Hartmann-Shack) wavefront sensing. Accurate measurements are possible with some of these techniques down to a fraction of a nanometer.

However, many of these techniques are difficult to apply to highly curved surfaces and/or optically transmissive surfaces. When objects such as, but not limited to, a contact lens, contact lens mold, high numerical aperture optical element, pin, optical lens, inter-ocular lens (IOL), IOL mold, curved mirror, cornea, or another object with a rapid variation in surface contour is measured, it is very difficult to project the light onto the entire surface and to collect it back in a controlled and uniform fashion. Projecting and collecting lens (es) with a very high numerical aperture (NA) are required. Furthermore, while good results may be achieved with some of these methods by projecting and then collecting the light from a spherical surface, the degree to which the surface can depart from spherical is limited by the dynamic range of the measurement instrument. This severely limits the range of objects whose surfaces can be measured since many objects are not spherical but may be highly aspherical.

Also, many objects are optically transmissive at the wavelength of the light used in the above-mentioned measuring systems. In that case, in projecting and collecting light from the object, light is collected from all surfaces simultaneously. The light reflected from various surfaces mixes together and makes interpretation of resulting patterns difficult. The different surfaces may reflect vastly different amounts of light depending upon the index of refraction and other conditions of the surfaces. While it is possible in some cases to spoil the reflection (or otherwise identify it) from the back surface (or other feature that is not of interest) by painting it black, immersing it in a fluid, or otherwise altering it, this has the effect of damaging the part that is being measured. This is not generally desirable in a measurement system.

It is also possible to use a contact profilometer to measure the surface. Very sophisticated versions of these instruments exist and they are capable of making very precise measurements. However, it is generally not possible to measure two surfaces simultaneously with a profilometer, and the fact that there is a contact with the surface may damage the object. In addition, these instruments are very slow and may have different precision on rough surfaces than they do for smooth surfaces.

Neal et al. U.S. Pat. No. 6,184,974 ("Neal et al."), which is incorporated herein by reference in its entirety as if fully set forth herein, discloses a means for making measurements of a small area of at least one surface of a silicon wafer or other flat surface and for stitching these measurements together to form a measurement of the entire surface. Neal et al. uses overlap regions to connect the measurements together and eliminate any effects of instrument inaccuracy during the measurement process. This same technique has been applied to the measurement of large telescope mirrors with excellent success (Kiikka et al, "The JWST Infrared Scanning Shack Hartmann System: a new in-process way to measure large mirrors during optical fabrication at Tinsley," SPIE 2006).

It would be desirable to provide a method and system for measuring one or more geometric characteristics of an object having one or more highly curved, potentially aspheric and non-symmetric surfaces. It would also be desirable to provide a method and system for measuring one or more geometric characteristics of an object that has at least one substantially transparent surface, which can accurately distinguish between first and second surface reflections and provide accurate surface shape maps for each surface.

In one aspect of the invention, a method determines at least one geometric characteristic of an object having a first surface and a second surface. The method comprises: (a) adjusting a positional relationship between a first surface of the object and a light source to illuminate a subregion of the first surface of the object, whereby a portion of light illuminating the subregion of the first surface of the object passes through the object to the second surface of the object; (b) delivering light from the subregion of the first surface of the object to a wavefront sensor while blocking a majority of light from the second surface of the object from reaching the wavefront sensor; (c) determining a wavefront of light received from the subregion of the first surface with a wavefront sensor; (d) repeating steps (a) through (c) for a plurality of different subregions spanning a measurement region for the first surface of the object, where adjacent subregions have an overlapping portion; (e) stitching together the wavefronts determined in each execution of step (c) including derivatives of the wavefronts in the overlapping portions, to construct a wavefront of light received from the measurement region of the first surface of the object; and (f) determining at least one shape parameter of the first surface of the object from the constructed wavefront.

In another aspect of the invention, a system determines at least one geometric characteristic of an object. The system comprises: a light source; a wavefront sensor; an optical system adapted to deliver light from the light source to a surface to be measured of the object, and to deliver light from the surface to be measured of the object to the wavefront sensor, whereby a portion of the light delivered to the surface to be measured passes through the object to a surface of the object that is not being measured; a positioner adapted to adjust relative positions of the light source and the surface to be measured such that, at each relative position, the light from the light source is delivered onto a sub-region of the surface to be measured, and light from the sub-region of the surface to be measured is delivered to the wavefront sensor, the positioner adjusting the relative positions such that adjacent subregions have an overlap portion; and a processor adapted to stitch together wavefronts measured by the wavefront sensor for different sub-regions of the surface to be measured at the relative positions provided by the positioner, including using derivatives of wavefronts in overlap regions, to construct a wavefront of light received from a measurement region of the surface to be measured, wherein the optical system comprises an aperture for blocking a majority of light from the surface of the object not being measured from reaching the wavefront sensor.

In yet another aspect of the invention, a method determines at least one geometric characteristic of an object having a first surface and a second surface. The method comprises: (a) adjusting a positional relationship between a first surface of the object and a light source to illuminate a subregion of the first surface of the object, including at least one of: rotating the object with respect to the light source, rotating the light source with respect to the object, tilting the object with respect to the light source, and tilting the light source with respect to the object; (b) delivering light from the subregion of the first surface of the object to a wavefront sensor; (c) determining a wavefront of light received from the subregion of the first surface with a wavefront sensor; (d) repeating steps (a) through (c) for a plurality of different subregions spanning a measurement region for the first surface of the object, where adjacent subregions have an overlapping portion; (e) stitching together the wavefronts determined in each execution of step (c) including derivatives of the wavefronts in the overlapping portions, to construct a wavefront of light received from the measurement region of the first surface of the object; and (f) determining at least one shape parameter of the first surface of the object from the constructed wavefront.

In still another aspect of the invention, a system determines at least one geometric characteristic of an object, the system comprising: a light source; a wavefront sensor; an optical system adapted to deliver light from the light source to a surface to be measured of the object, and for delivering light from the surface to be measured of the object to the wavefront sensor; a positioner adapted to adjust relative positions of the light source and the surface to be measured such that, at each relative position, the light from the light source is delivered onto a sub-region of the surface to be measured, and light from the sub-region of the surface to be measured is delivered to the wavefront sensor, the positioner adjusting the relative positions such that adjacent sub-regions have an overlap portion, wherein the positioner includes one of: means for rotating the light source, means for rotating the object, means for tilting the light source, and means for tilting the object; and a processor adapted to stitch together wavefronts measured by the wavefront sensor for different sub-regions of the surface to be measured at the relative positions provided by the positioner, including using derivatives of wavefronts in overlap regions, to construct a wavefront of light received from a measurement region of the surface to be measured.

In a further aspect of the invention, a system determines at least one geometric characteristic of an object having a first surface and a second surface. The system comprises: a light source adapted to illuminate the object; an optical element adapted to receive light from the first and second surfaces of the object and to produce a first light beam corresponding to light from the first surface and a second light beam corresponding to light from the second surface; a light intensity detector having a radiation sensitive surface adapted to receive the first and second light beams and to detect the intensity of incident radiation on the radiation sensitive surface from the first and second light beams, and to produce an output that provides a measure of the intensity of the incident radiation; a positioner adapted to adjust relative positions of the optical element and the light intensity detector; and a processor adapted to determine wavefronts of the light from the first and second surfaces based on the output of the light intensity detector at a plurality of different relative positions.

In a still further aspect of the invention, a method determines at least one geometric characteristic of an object having a first surface and a second surface. The method comprises: (a) illuminating the object; (b) transmitting light from the first and second surfaces of the object through an optical element to produce a first light beam corresponding to light from the first surface and a second light beam corresponding to light from the second surface; (c) detecting the intensity of incident radiation on a radiation sensitive surface from the first and second light beams; (d) adjusting relative positions of the optical element and the radiation sensitive surface, and at each of a plurality of different relative positions producing an output that provides a measure of the intensity of the incident radiation; and (e) determining wavefronts of the light from the first and second surfaces of the object based on the outputs produced at each of the different relative positions.

In yet a further aspect of the invention, a system determines at least one geometric characteristic of an object having a first surface and a second surface. The system comprises: a light source adapted to illuminate the object; a diffractive optical element adapted to receive light from the first and second surfaces of the object and to produce therefrom at least two spatially-separated light distributions having at least one statistical characteristic different from each other; a light intensity detector having a radiation sensitive surface adapted to receive the at least two spatially-separated light distributions, to detect the at least two spatially-separated light distributions at different points across the radiation sensitive surface, and to produce an output that provides a measure of the intensity of the incident radiation at the different points; and a processor adapted to determine wavefronts of the light from the first and second surfaces based on the output of the light intensity detector.

In still yet another aspect of the invention, a method determines at least one geometric characteristic of an object having a first surface and a second surface. The method comprises: (a) illuminating the object; (b) transmitting light from the first and second surfaces of the object through a diffractive optical element to produce therefrom at least two spatially-separated light distributions having at least one statistical characteristic different from each other; (c) detecting the intensity of incident radiation on a radiation sensitive surface from the at least two spatially-separated light distributions at different points on the radiation sensitive surface to produce an output that provides a measure of the intensity of the incident radiation at the different points; (d) determining wavefronts of the light from the first and second surfaces of the object based on the output of the detection.

In still yet a further aspect of the invention, a system determines at least one geometric characteristic of an object. The system comprises: a structure having a reference surface with a known curvature; a stage adapted to hold an object; and an interferometer. The interferometer comprises: a light source adapted to generate light having a broad spectral bandwidth, a detector; a mirror; a beamsplitter adapted to receive the light from the light source and to divide the light into a first portion and a second portion; wherein the system is configured to provide the first portion of the light from the beamsplitter to illuminate the object and the reference surface, and to provide at least some of the first portion of the light from the object and the reference surface to the detector, and wherein the system is configured to provide the second portion of the light from the beamsplitter to illuminate the mirror, and to provide at least some of the second portion of the light from the mirror to the detector; and means for adjusting an optical path length traveled by the second portion of the light from the beamsplitter to the detector, wherein the detector is adapted to output a signal indicating when an optical path length traveled by the first portion of the light from the beamsplitter to the detector is the same as the optical path length traveled by the second portion of the light from the beamsplitter to the detector.

In another, further aspect of the invention, a method determines at least one geometric characteristic of an object. The method comprises: (a) generating light having a broad spectral bandwidth; (b) dividing the light into a first portion and a second portion with a beamsplitter; (c) providing the first portion of the light to a selected region of the object and to a reference surface of a structure having a known curvature; (d) providing at least some of the first portion of the light from the object and the reference surface to a detector; (e) providing the second portion of the light to a mirror; (f) reflecting the first portion of the light from the mirror to the detector; (g) passing a second portion of the light through a reference lens to a selected region of a surface to be measured of the object; (h) adjusting an optical path length traveled by the second portion of the light from the beamsplitter to the detector until the detector outputs a signal indicating a first interference fringe caused by light refracted or reflected by a first surface of the object; (i) adjusting the optical path length traveled by the second portion of the light from the beamsplitter to the detector until the detector outputs a second signal indicating a second interference fringe caused by light refracted or reflected by a second surface of the object; (j) adjusting the optical path length traveled by the second portion of the light from the beamsplitter to the detector until the detector outputs a second signal indicating a third interference fringe caused by light refracted or reflected by the reference surface; and (k) determining a thickness of the object at the selected region from the first, second, and third interference fringes.

DETAILED DESCRIPTION

As discussed above, it is desirable to characterize one or both surfaces of an optically transparent object, or an object having at least one substantially transparent surface, however, in general it is difficult to separate the reflection from the front surface from that of the back surface. However, in the case of a highly curved surface, such as is typical of a contact lens, contact lens mold, aspheric optic, IOL, cornea or other highly curved object, we disclose below systems and methods for separating the two surfaces in order isolate the surfaces for measurement and/or to measure the two surfaces (either sequentially or simultaneously).

Figure 1A:
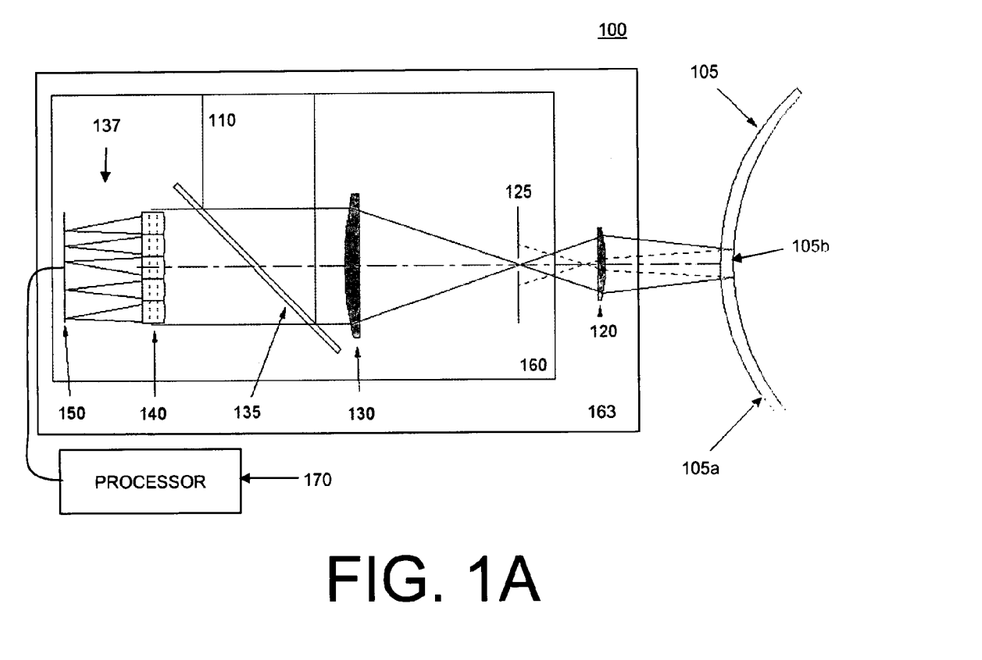
FIGS. 1A-B functionally illustrate in block-diagram form one embodiment of a system for determining at least one geometric characteristic of an object.
Figure 1B:
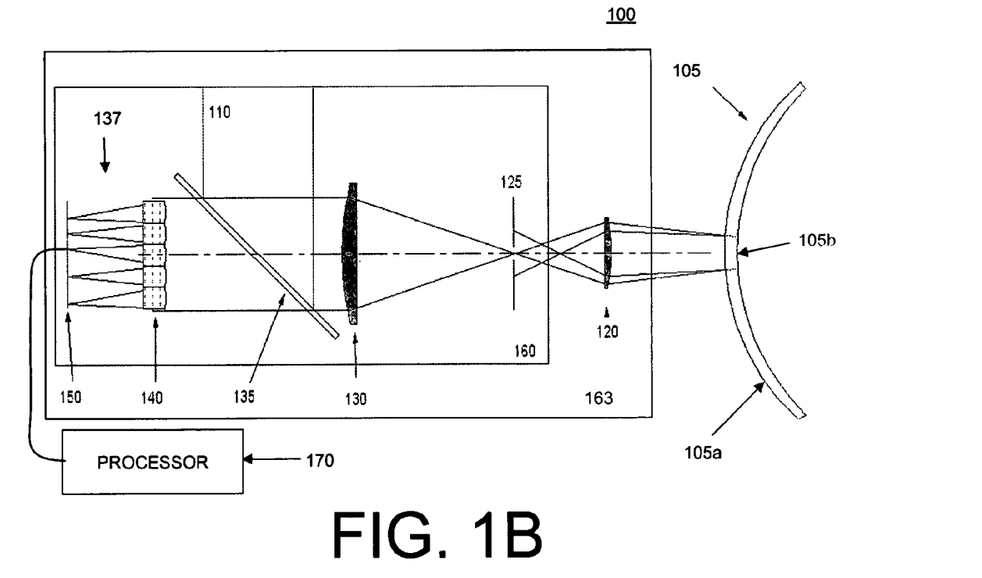

FIGS. 1A-B functionally illustrate one embodiment of a geometric measurement system 100 for determining at least one geometric characteristic of an object 105, and an associated method of determining at least one geometric characteristic of the object 105, using a wavefront sensor. In particular, the system and method illustrated in FIGS. 1A-B are well suited for determining one or more geometric characteristics of a substantially optically transparent object 105 having a highly curved surface, such as a contact lens. Geometric characteristic(s) of the object 105 that may be characterized by the system 100 include shapes of one or both main surfaces 105a, 105b and/or a thickness profile of the object 105.

Geometric measurement system 100 includes: a light source 110; an optical system comprising lenses 120 and 130, and a modulator or spatial filter 125 disposed in an optical path between lenses 120 and 130; a beamsplitter 135; a wavefront sensor 137 including lenslet array 140 and detector 150; a positioner 163; a secondary positioner 160; and a processor 170.

Beneficially, light source 110 is adapted to produce collimated light. Also beneficially, light source 110 is a pulsed light source, which may be operated under control of processor 170. The light source 110 may mounted separately from the positioners 160, 163 or, alternatively, may be configured to have a fixed position relative to one of the positioners 160, 163. It will be appreciated that the light source 110, as well as other light sources discussed herein, may be replaced by a source of electromagnetic radiation outside the visible wavelength band, for example, in the near-infrared, infrared, or ultraviolet bands. While the light source 110 will generally be with a relatively narrow wavelength band, for example, a laser or LED, the light source 110 may also include broadband sources.

Beneficially, spatial filter 125 operates to block a majority (i.e., ≧50%) of the reflected and/or refracted light from a surface of object 105 not being characterized or measured from reaching wavefront sensor 137. Depending upon various factors, including for example the characteristics of the surfaces of the object being measured, spatial filter 125 may operate to block a substantial majority (i.e., ≧90%) of the reflected and/or refracted light from the surface of object 105 not being characterized or measured from reaching wavefront sensor 137. In one embodiment, as illustrated in FIGS. 1A-B spatial filter 125 may be an aperture, particularly a range limiting aperture (RLA), having a size adapted to operate in conjunction with lens 130 and positioner 163 to pass substantially all of the light reflected or refracted from a surface of object 105 that is being measured or characterized, and to block a majority or a substantial majority of the reflected or refracted light from a surface of object 105 not being characterized or measured from reaching wavefront sensor 137.

Alternatively, spatial filter 125 may be a spatial light modulator (such as a transmissive liquid crystal device), or other device that can spatially filter or modulate a light beam.

Beneficially, lenses 120 and 130 are mounted in an arrangement to provide an adjustable telescope, for example by means of secondary positioner 160.

As shown in FIGS. 1A-B, beneficially wavefront sensor 137 is a Shack-Hartman wavefront sensor. However, a moiré deflectometer, a Tscheming aberrometer, or other suitable sensor or interferometer could be employed.

Positioner 163 is adapted to adjust the relative positions between: (A) light source 110 and/or wavefront sensor 137 and/or spatial filter 125; and (B) object 105, in particular a surface of the object 105 that is being characterized or measured. As used herein, the term "positioner" means a device that is used to control at least one linear and/or rotational position of objects or elements attached to the positioner. In some embodiments, the positioner provides up to six axes of control (e.g., 3 linear axes and three rotational axes). Beneficially, positioner 163 adjusts these relative positions such that, at each relative position, light from light source 110 is delivered onto a subregion of the surface to be measured, and light scattered and/or reflected from the subregion of the surface to be measured is delivered to wavefront sensor 137. Positioner 163 adjusts the relative positions such that adjacent subregions scanned on the surface of object 105 have an overlap portion. Positioner 163 may include its own controller, or may be controlled by processor 170.

Beneficially, positioner 163 is adapted to rotate and/or tilt the optical system in a goniometrical manner about the center of curvature of the surface of object 105 being measured, and performs measurements over a plurality of subregions spanning a desired measurement region (which may be the entire surface of object 105) as will be explained in further detail below. Positioner 163 also serves to adjust the relative distance between the measurement system and the first or second surfaces (e.g., the spacing or distance between spatial filter 125 and object 105).

Turning to FIG. 1A, to begin a measurement of object 105, positioner 163 is controlled to adjust a positional and/or rotational relationship between first surface 105a of object 105 and light source 110 and/or spatial filter 125 and/or wavefront sensor 137 to illuminate a desired subregion of first surface 105a.

Collimated light from light source 110 is injected via beamsplitter 135 and through the relay telescope of lenses 130 and 120. The light is injected through the spatial filter 125 which in the illustration of FIGS. 1A-B is shown as an RLA arranged to be one focal length from lens 130. Light from lens 130 illuminates a sub-region of first surface 105a of object 105. Beneficially, the position of lens 120 and/or lens 130 is adjusted so that light reflected from first (e.g. front) surface 105a of object 105 just matches the convergence (or divergence) of the incident light. Thus, the reflected rays from the subregion of front surface 105a of object 105 retrace (approximately) their injected path and pass back through spatial filter 125.

The portion of the light that is transmitted through optically transparent object 105 is focused by the curvature of surface 105a, and after reflection from the second surface 105b of element 105, is further defocused. This light is collected also by lens 120 but is mostly blocked by spatial filter 125 from reaching wavefront sensor 137, since it is not focused in the plane of spatial filter 125. A small portion of this light will pass through spatial filter 125 and be imaged through lens 130, passing through beamsplitter 135, lenslet array 140 onto detector 150. Since spatial filter 125 blocks a majority or a substantial majority of the light from second surface 105b of object 105, the light or signal from first surface 105a on detector 150 will generally be much brighter and will be straightforward to identify.

Detector 150 operates in conjunction with processor 170 to determine a wavefront of light received by the wavefront sensor 137 from the subregion of first surface 105a of object 105.

Positioner 163 then readjusts the relative position and/or angle between: (A) light source 110 and/or spatial filter 125 and/or wavefront sensor 137; and (B) the surface of object 105 to be measured to illuminate another subregion of the object's first surface 105a, and wavefront sensor 137 then measures the wavefront from this new subregion. At this time, beneficially the relay telescope comprising lenses 120 and 130 may be adjusted to maintain the focus of the light on the desired subregion of surface 105a by adjusting secondary positioner 160, for example by adjusting the convergence or divergence of light directed toward the object 105. This allows for the dynamic range of wavefront sensor 137 to be greatly extended with respect to defocus error, which for highly curved surfaces is usually the dominant error term. There is a unique relationship between the position of secondary positioner 160 that controls the separation of lenses 120 and 130 and the amount of defocus error (also known as spherical optical power) that is introduced. The amount of defocus, which can be determined by reading out the position of secondary positioner 160 with encoders or some other method, is added to the measured wavefront error from wavefront sensor 137 comprised of lenslet array 140 and detector 150. Thus even when the surface of object 105 being measured is highly aspheric and may change its optical power or curvature rapidly over a small distance, it is possible to readjust the position of secondary positioner 160 as positioner 163 scans over different subregions, and always stay within the dynamic range of the combined optical system and wavefront sensor 137.

Figure 2:
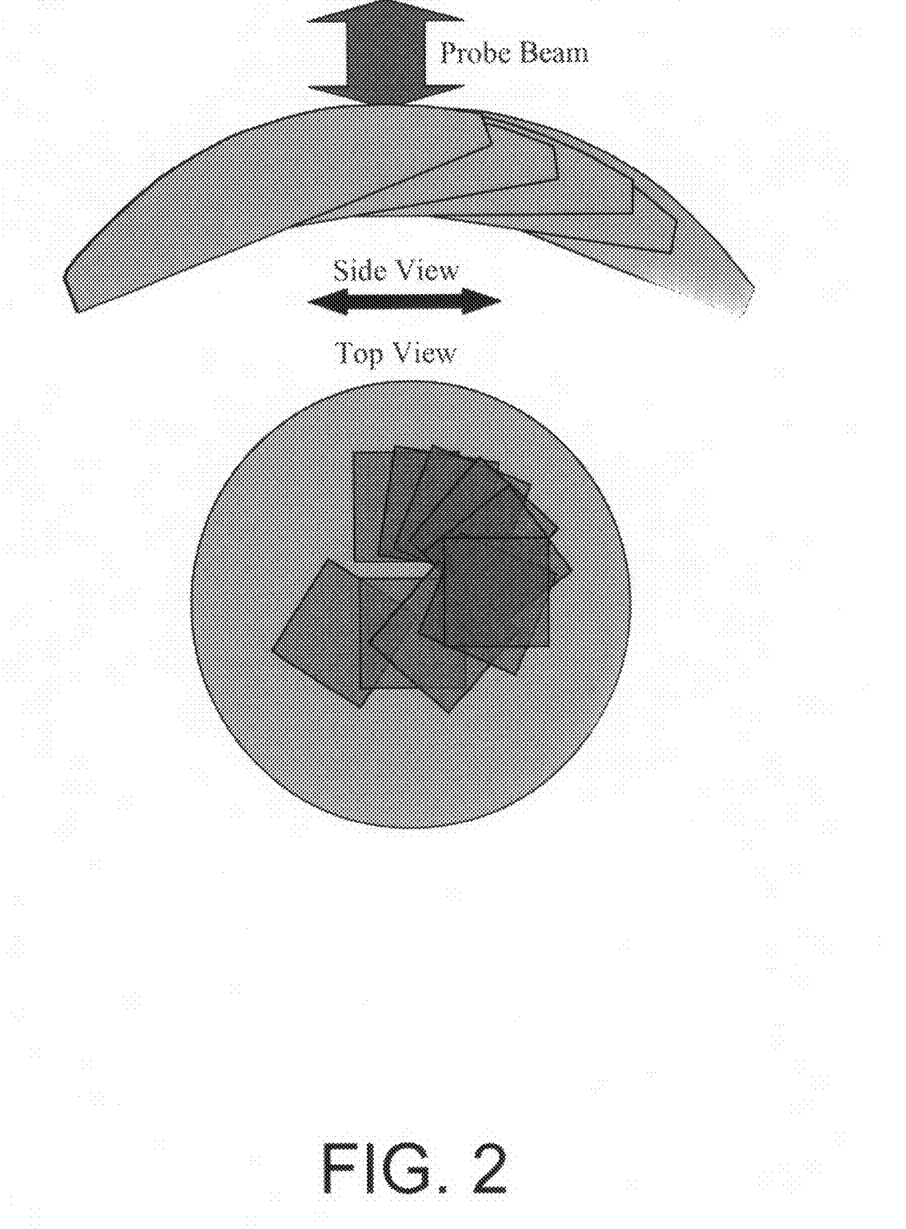
FIG. 2 functionally illustrates a process of measuring wavefronts from a number of subregions of an object and stitching the wavefronts together to obtain a wavefront from a larger region of the object spanning at least portions of the subregions.

FIG. 2 illustrates a process of measuring wavefronts from a plurality of subregions of object 105, which wavefronts are then stitched together by processor 170 to construct a wavefront of light received from a larger region of object 105 spanning at least portions of the subregions. Beneficially, as illustrated in FIG. 2, the subregions each include an overlap portion that is "shared" with another adjacent subregion. Positioner 163 can be controlled to produce a pattern of known sample regions. This pattern can be regular or irregular, so long as the exact measurement region of each is known. Further details of the process of stitching together the individual wavefronts of subregions to construct a wavefront of a larger region are disclosed in Neal et al. U.S. Pat. No. 6,184,974, which has already been incorporated herein by reference.

Turning now to FIG. 1B, to measure or characterize second surface 105b of object 105, the relative distance between the object 105 and lens 120 and/or spatial filter 125 is adjusted until the light reflected from second surface 105b passes through the spatial filter 125 by retracing its path through the optical system 120, 125, and 130 (e.g., by using positioner 163 to move the system 100 toward the object 105). In this specific embodiment, secondary positioner 160 may also be adjusted to modify the convergence (or divergence) of light directed from the lens 120 and towards the object 105, such that light reflected or refracted from a desired subregion of second surface 105b is delivered to wavefront sensor 137, while a majority (i.e., ≧50%), or even perhaps a substantial majority (i.e., ≧90%), of light from first surface 105a is now blocked by spatial aperture 125 from reaching wavefront sensor 137. The correct position can be found, for example, by monitoring the focal spot brightness on the detector 150 and searching for a second brightness peak, or by looking for some feature in the wavefront as reconstructed by wavefront sensor 137. This may be the position where the collimation of light into the wavefront sensor 137 has reached a predetermined value or even where the light is completely collimated. At this time, the reflection from front surface 105a is not in focus at spatial filter 125 and so spatial filter 125 blocks a majority or a substantial majority of this light.

In one embodiment, surfaces 105a and 105b are measured by making two passes, one over each of the two surfaces 105a, 105b (moving system 100 and/or object 105 goniometrically as described earlier and illustrated in FIG. 2), and then calculating the thickness of object 105 from the amount that positioner 163 was moved between the two passes. The surface shape of front surface 105a and index of refraction of the material comprising object 105 are taken into account when determining the shape of second surface 105b.

In another embodiment, surfaces 105a and 105b are measured by sequentially in each subregion by moving positioner 163 in the direction approximately normal to the surfaces, then moving to a new subregion and repeating the measurement of both surfaces.

Figure 3A:
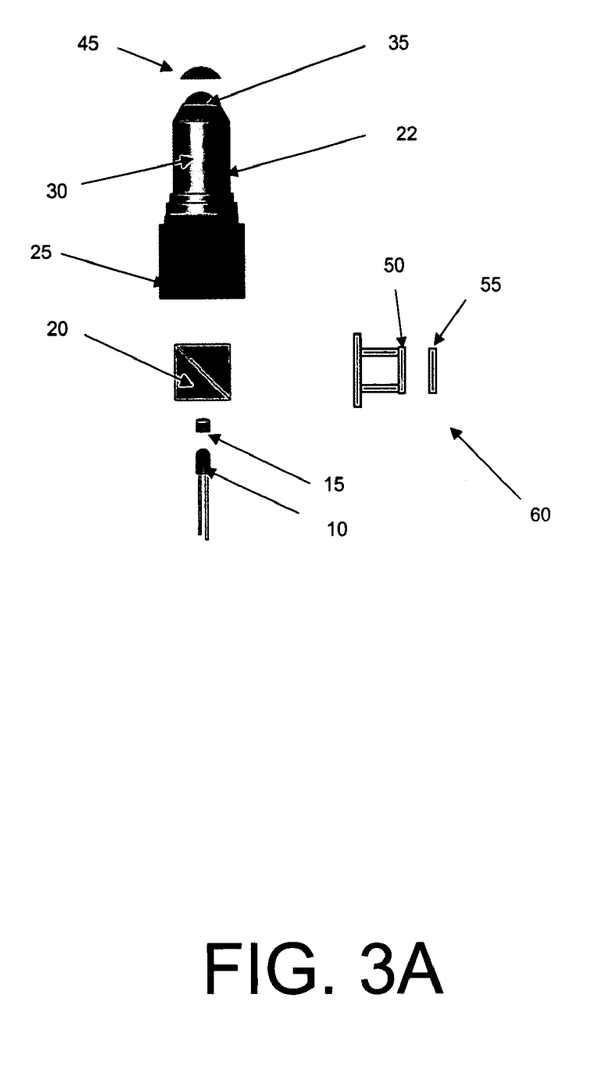
FIGS. 3A-B illustrate two possible arrangements for a geometric measurement system which may be one physical implementation of geometric measurement system of FIGS. 1A-B.
Figure 3B:
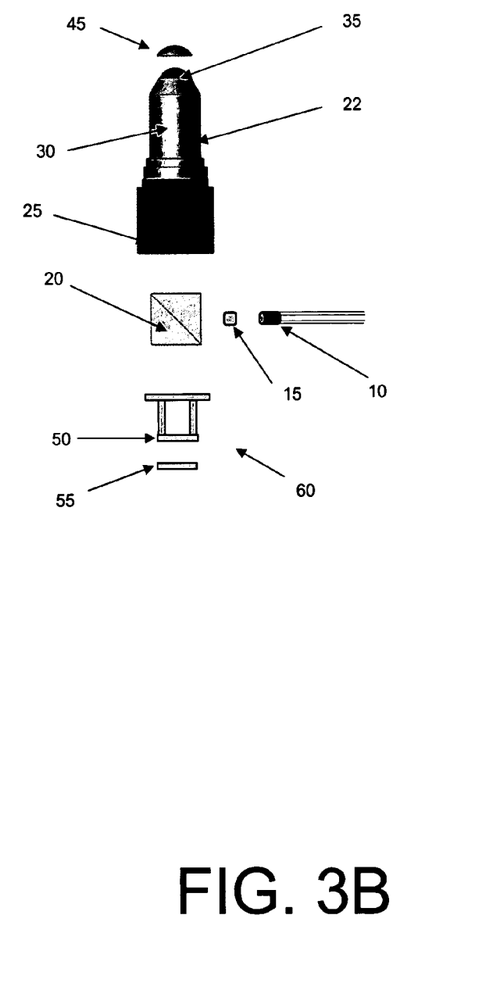

FIGS. 3A-B illustrate two exemplary arrangements for a geometric measurement system which may be employed for geometric measurement system 100. The arrangements of FIGS. 3A-B each include: light emitting element 10 (e.g., an LED or diode laser in the visible, near-infrared, infrared, or ultraviolet wavelength bands of the electromagnetic spectrum) and collimator 15 as a light source; beamsplitter 20; microscope assembly 22 including image relay lens 25, pinhole (aperture) 30 (not visible in FIGS. 3A-B), objective lens 35; and sensor 60, comprising an optical element 50 and a detector array (e.g., a charge-coupled device (CCD)) 55. Element 45 is an object under measurement.

Operationally, light from light emitting element 10 is collected by collimating lens 15 and projected through beamsplitter 20. This light is further collected by image relay lens 25 and focused onto pinhole 30 and recollected by microscope objective lens 35. This produces a small beam, coincident with a desired subregion of object 45, that is then projected onto the highly curved surface of object 45 that is being measured. Light from both surfaces of object 45 may be reflected from object 45 and collected by the objective lens 35. However, the shape of object 45 will cause the light from the surface that is not being measured to arrive at the objective lens 35 at significantly different divergence from the light reflected off the first surface that is being measured. The light from the surface not being measured thus arrives at aperture 30, which is arranged to be about one focal length away from the objective lens 35, and creates a fairly large spot at this plane. Thus aperture (pinhole) 30 spatially filters a majority (i.e., $\geq 50\%$) of the light from the unwanted surface that is not being measured from reaching sensor 60. Beneficially, aperture 30 spatially filters a substantial majority (i.e., $\geq 90\%$) of the light from the unwanted surface that is not being measured from reaching sensor 60. The light that passes through aperture 30 then is recollected by relay image lens 25, and reflects off beamsplitter 20 onto sensor 60.

In the case of a physical implementation of geometric measurement system 100, then sensor 60 may be a Shack-Hartmann wavefront sensor, wherein optical element 50 is a lenslet array that generates light spots that are focused on detector array 55. In that case, detector array 55 detects the focal points of the light spots produced by lenslet array 50 to determine a wavefront of light received back from object 45. Beneficially, the output of detector 60 is provided to a processor (not shown in FIGS. 3A-B), such as processor 170 in FIGS. 1A-B. Wavefronts from a plurality of subregions of object 45 are then stitched together to form a combined wavefront for a larger region (perhaps an entire surface area) of object 45, as described above.

In some systems, it may be advantageous to mount relay lenses 25 and 35 in an arrangement that would permit adjustment of their relative spacing. This would allow the system to adjust the base defocus to match that of the local region of the part to be tested. For highly aberrated, aspheric, or rapidly varying parts this may be advantageous. Other arrangements are also possible, and may be employed by those that are skilled in the art.

Various modifications to the arrangements shown in FIGS. 3A-B are possible, and some of these will be described in further detail below with respect to other embodiments of a geometric measurement system.

Figure 4A:
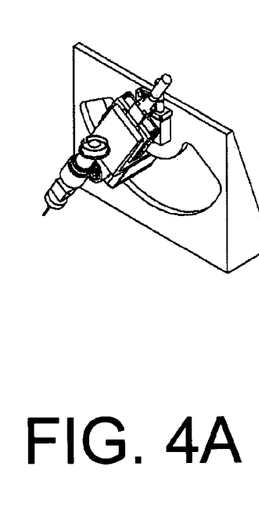
FIGS. 4A-C illustrate a geometric measurement instrument, including a goniometer, that may be one structural embodiment of the arrangement of FIG. 3A.
Figure 4B:
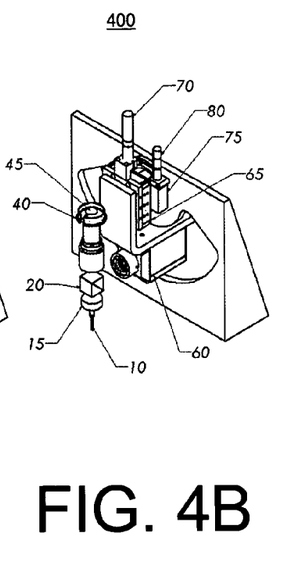
Figure 4C:
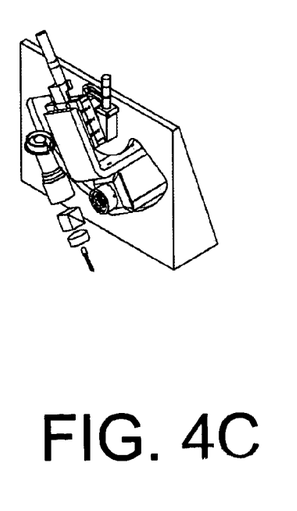

FIGS. 4A-C illustrate geometric measurement instrument 400, including a goniometer, that may be one structural embodiment of the arrangement of FIG. 3A.

In FIGS. 4A-C, the elements depicted in FIG. 3A are shown mounted on a moving platform 65. In this case the object under test 45 is mounted in a test cell 40 which is arranged so that it can rotate freely under computer control. Light source 10, collimating lens 15, beamsplitter 20, the microscope objective assembly, and sensor 60 are mounted on a common platform and held rigidly in place. Beneficially, the platform may be rapidly rotated about its axis of symmetry.

In one case, geometric measurement instrument 400 may be an embodiment of geometric measurement system 100. In that case, sensor 60 is a wavefront sensor, beneficially a Shack-Hartmann wavefront sensor (although a moiré deflectometer, a Tscheming aberrometer, or other appropriate sensor could be employed instead). Also in that case, geometric measurement instrument 400 measures only one surface of object 45 at time and filters the light from the other surface. So it is necessary to have a stage the can be adjusted so that the appropriate plane is correctly imaged by the optical system. Accordingly, adjustment 70 permits adjustment of the radius of curvature that can be correctly read. The overall positioning of geometric measurement instrument 400 is accomplished with the goniometric part 75 controlled through actuator 80. This rotates the measurement head through an angle "goniometrically" about the center of curvature of some axis of object 45. Since the part 40 is also rotated by rotating holder 45, the entire part may be scanned by rotating the part with holder 45 through on full revolution while measuring the subregions with the sensor 60, then adjusting the goniometer by an incremental rotation, rotating the part through a full revolution while measuring, etc.

Figure 5A:
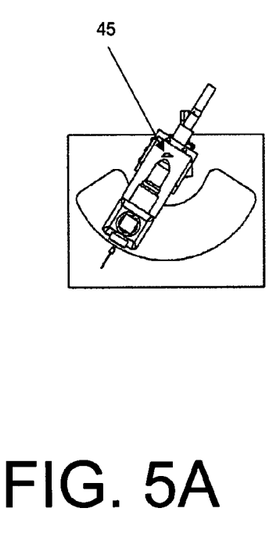
FIGS. 5A-C are front views illustrating operation of the goniometer of FIGS. 4A-C.
Figure 5B:
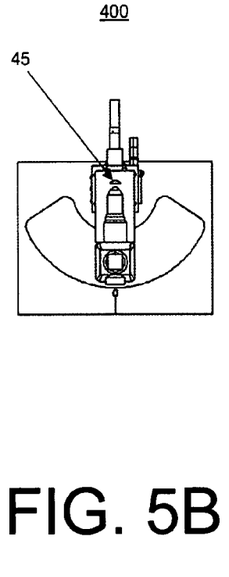
Figure 5C:
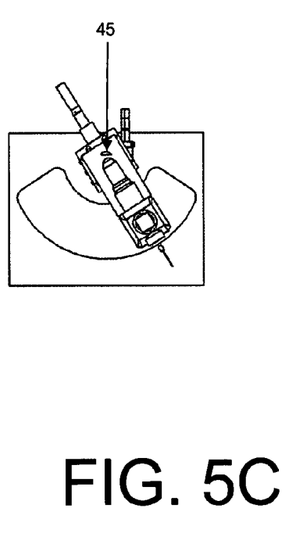

FIGS. 5A-C are front views illustrating operation of geometric measurement instrument 400 of FIGS. 4A-C, including a goniometer. It can be seen that geometric measurement instrument 400 measures only a small subregion of object 45 at a time. Beneficially, geometric measurement instrument 400 is arranged with encoders on the motor axes. In this embodiment it is possible to use these encoders to issue pre-arranged triggers to a processor (e.g., processor 170 of FIGS. 1A-B) at certain stage positions or angles. The triggers initiate the action of sending a pulse of light from light emitting device 10 and detecting the received light from object 45 at sensor 60. Beneficially, light emitting device 10 and sensor 60 are synchronized together. It is also possible to have only light emitting device 10 or only sensor 60 operate in a pulsed mode.

Figure 6:
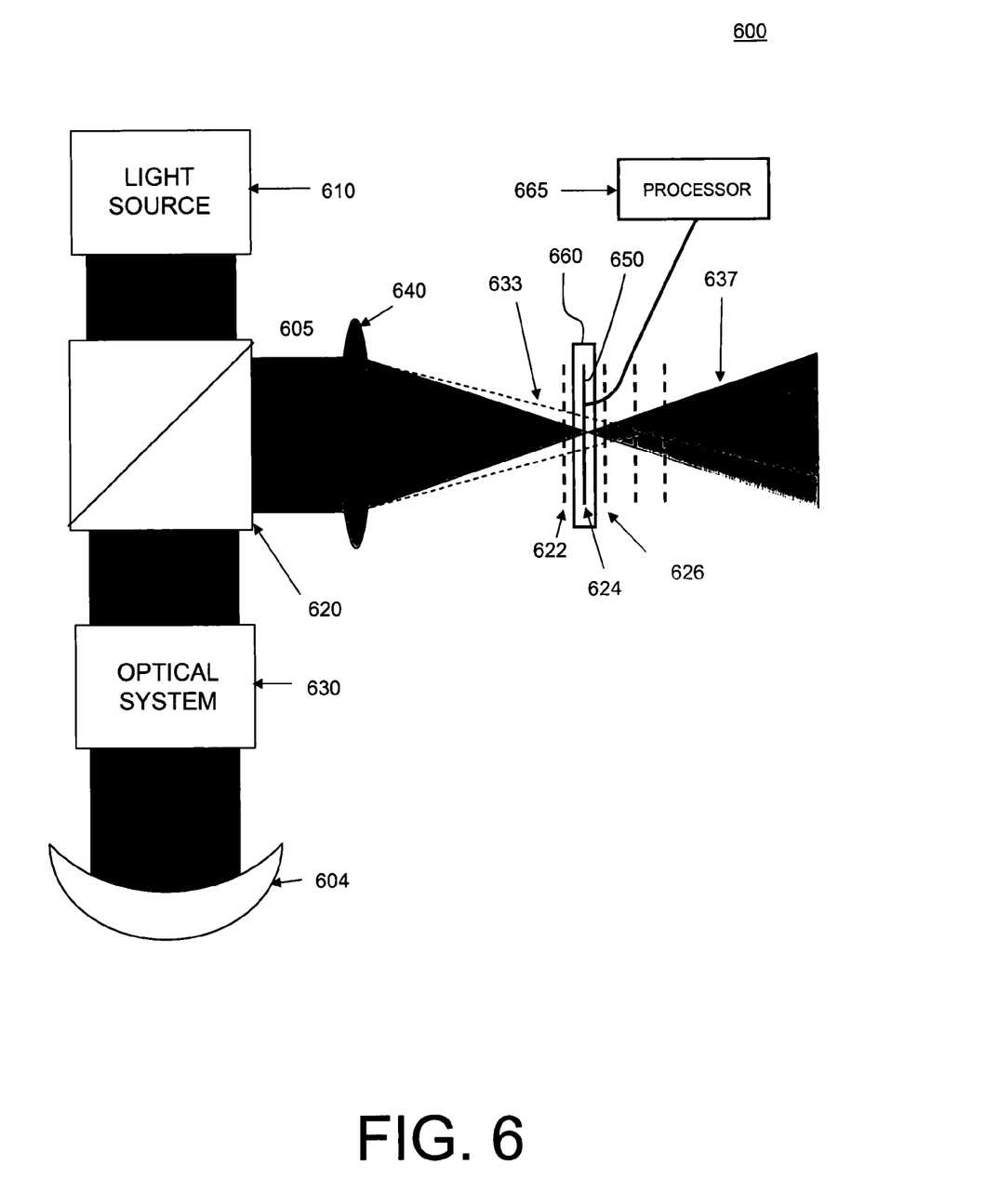
FIG. 6 illustrates another embodiment of a system for determining at least one geometric characteristic of an object.

FIG. 6 illustrates still another embodiment of a geometric measurement system 600 for determining at least one geometric characteristic of an object 604, and an associated method of determining at least one geometric characteristic of the object 604, using a phase diversity sensor.

Geometric measurement system 600 includes a light source 610 (or other source of electromagnetic radiation); a beamsplitter 620; an optical system 630; an optical element (e.g., lens and/or diffractive optical element) 640; a detector 650; a positioner 660; and a processor 665.

Optical element 640, detector 650 of electromagnetic radiation, and positioner 660 form a phase diversity sensor. The phase diversity sensor is a wavefront sensor that tracks the distribution of light intensity from an initial pupil through the measurement of the irradiance distribution at a number of discrete planes.

Operationally, an input wavefront 605, which can consist of light that has been reflected from multiple surfaces of object 604, is incident upon optical element 640. Optical element 640 collects the light and directs it towards a focus. However, since there are two (or more) fields present in wavefront 605, the light will create two (or more) separate optical beams 633 and 637 which reach focus at different points along the z-axis. By acquiring and recording multiple irradiance distributions at different planes 622, 624 and 626 (and others as needed) using positioner 660, the essential information about how the light propagates from plane to plane is used to determine the incident wavefront 605. In general it takes measurement in at least two planes, but measurement in more planes may give better analysis of the data.

In the case where object 604 to be measured is a contact lens having two surfaces, optical element 640 receives light from the first and second surfaces of object 604 and produces a first light beam corresponding to light from the first surface and a second light beam corresponding to light from the second surface. Detector 650 has a radiation sensitive surface. Detector 650 receives the first and second light beams and detects the intensity of incident radiation on the radiation sensitive surface from the first and second light beams. Detector 650 produces an output that provides a measure of the intensity of the incident radiation. Positioner 660 adjusts relative positions of optical element (e.g., lens) 640 and light intensity detector 650. Processor 665 determines wavefronts of the light from the first and second surfaces of object 604 based on the output of light intensity detector 650 at a plurality of different relative positions.

One advantage of geometric measurement system 600 is that it can measure two surfaces of object 640 practically simultaneously and determine both the radius of curvature of each surface and the separation between the surfaces (thickness).

In general it may be inconvenient to make measurements while moving a detector or using multiple beam splitters to dissect the light in multiple directions. Thus it may be preferable to separate the planes of the optical beams across the detector instead of moving the detector.

Figure 7:
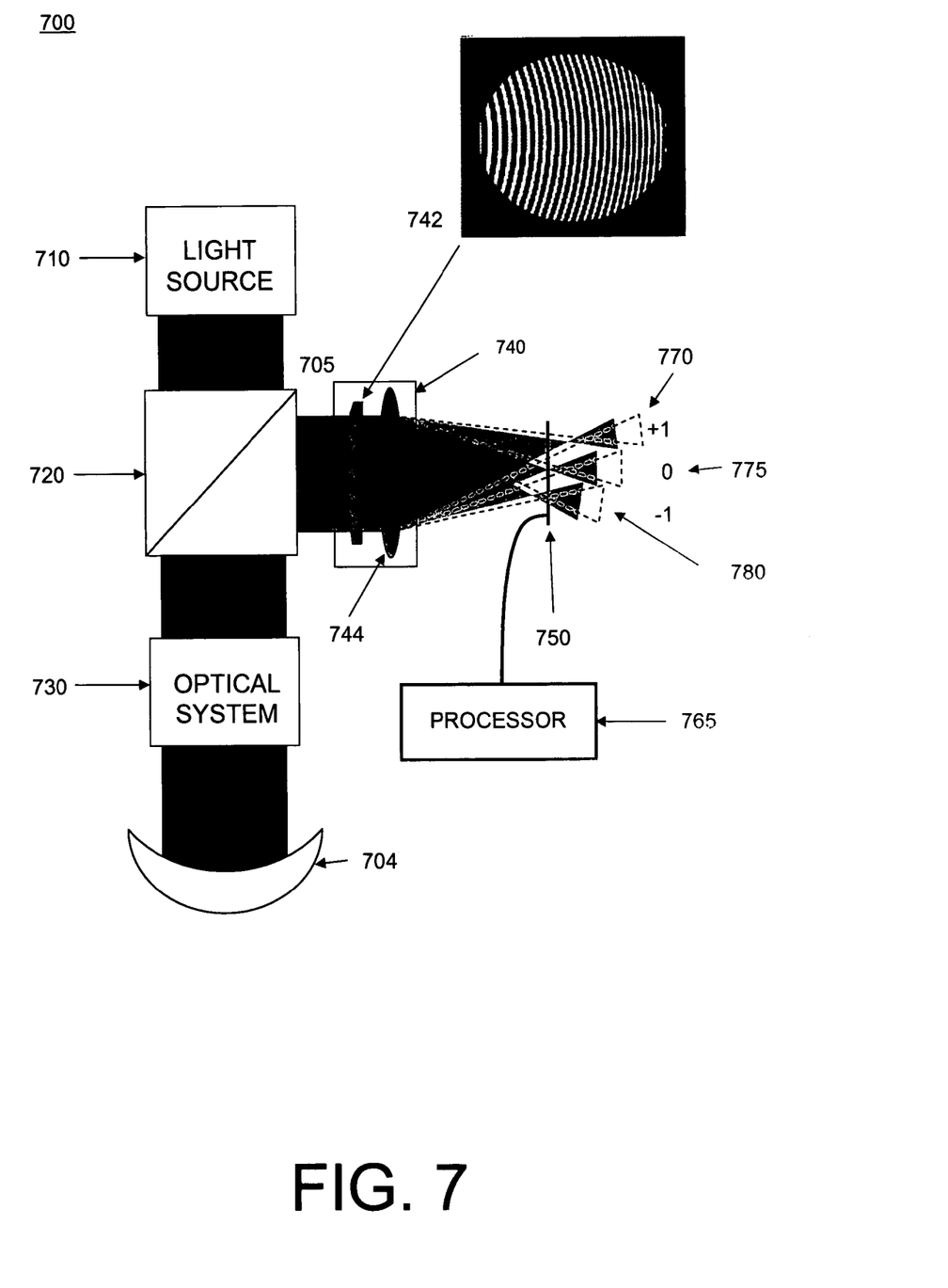
FIG. 7 illustrates yet another embodiment of a system for determining at least one geometric characteristic of an object.

Accordingly, FIG. 7 illustrates yet another embodiment of a geometric measurement system 700 for determining at least one geometric characteristic of an object 704, and an associated method of determining at least one geometric characteristic of the object 704, using a phase diversity sensor.

Geometric measurement system 700 includes a light source 710; a beamsplitter 720; an optical system 730; a diffractive optical element 740; a light intensity detector 750; and a processor 765. Beneficially, diffractive optical element 740 includes a diffraction grating 742 configured to provide a plurality of diffraction orders and a lens 744, which could be combined into a single physical component.

Operationally, an input wavefront 705, which can consist of light that has been reflected from multiple surfaces of object 704, is incident upon diffraction grating 742 which has some defocus fringes added to the grating lines. Light that is diffracted by this grating will be diffracted into a +1 diffraction order 770 and a −1 diffraction order 780 (and other orders depending on the exact structure of the grating). Some light will be undiffracted and hence stay in a zeroth diffraction order 775. In one example, the +1 order 770 has an effective negative focal power and the light spreads but also has net tilt, and the −1 order 780 has a positive focal power and so the light is concentrated, also with net tilt in the other direction. Optical element (e.g., a refractive or diffractive lens) 744 is included to create a compact instrument, but can be omitted at the expense of a resultantly longer instrument. As noted above, is also possible to build the power of the lens into diffraction grating 742. Thus the light that is collected at a single plane 725 has three different, spatially separated images. The first image 770 is light that propagates past light intensity detector 750. It is like plane 630 in the FIG. 6. Light from the 0 order 775 is at the main focus and is similar to plan plane 625 in the FIG. 6, while light from the −1 order 780 is analogous to plane 620. Here, the images are spatially separated and therefore may conveniently be acquired simultaneously. This arrangement may find particular benefit when one of the surfaces of object 704 has a particularly weak reflection. For example, one of the surfaces may have an anti-reflective coating or may be in contact with another element (not shown) that has a similar refractive index to that of object 704. Such may be the case when the object is the cornea of an eye or part of a compound lens, such as an achromat lens.

By processing the sub images mathematically, the reflected wavefronts from both surfaces of an object (e.g., a contact lens) can be determined. With a more sophisticated diffractive optic 744 it is possible to create even more images and hence derive a more accurate estimate of the incident wavefronts. Further details of the calculation of a surface shape using a phase diversity sensor may be found in Greenaway et al. U.S. Patent Publication 20060175528, the entirety of which is hereby incorporated herein by reference in its entirety as if fully set forth herein.

Beneficially, the exemplary arrangements shown in FIGS. 3A-B may be employed for geometric measurement system 700, with the modification that microscope assembly 22 omits the aperture (pinhole) 30.

In that case, light is injected via beamsplitter 20 and passes through microscope assembly 22 where it is directed onto the surfaces of object 45. The optical head rotates in a goniometrical fashion about the focal plane of object 45 and performs the measurement with the assistance of sensor 60, which in this case is a phase diversity sensor. Sensor 60 comprises a CCD camera with a lens and diffraction grating placed in front; so, conceptually, it looks very much like a wavefront sensor. The phase diversity sensor uses a diffraction grating with a specially curved grating field to create images before and after a focal plane. This allows different parts of a 3D object to be measured simultaneously.

Figure 8:
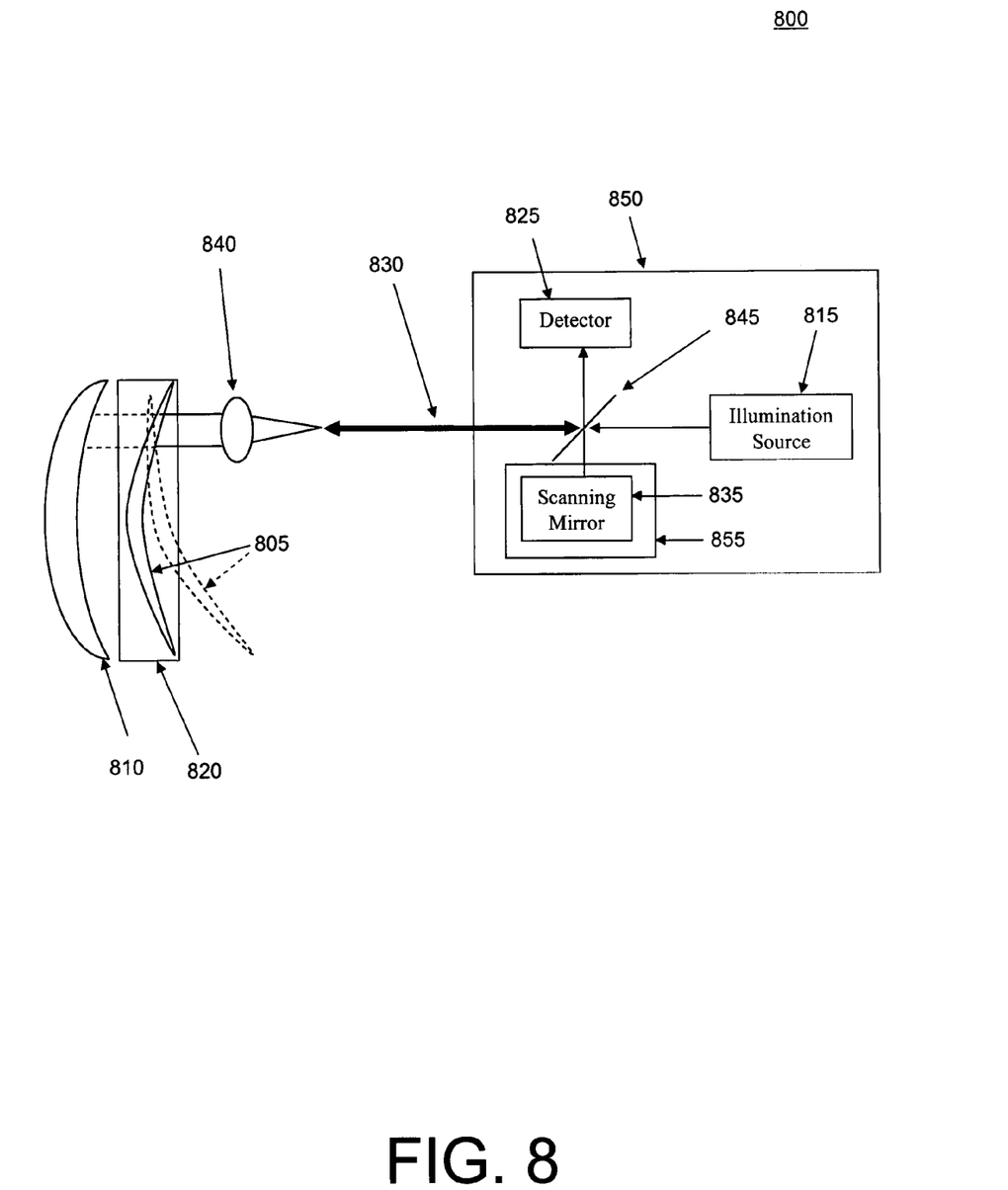
FIG. 8 illustrates still another embodiment of a system for determining at least one geometric characteristic of an object.

FIG. 8 shows a block diagram of yet another embodiment of a geometric measurement system 800 for determining at least one geometric characteristic of an object 805, and an associated method of determining at least one geometric characteristic of the object 805, using a white light interferometer.

Geometric measurement system 800 includes: a structure 810 having a reference surface with a known curvature; a stage 820 adapted to hold object 805; an optical fiber 830; a collimating lens 840; and an interferometer 850. Interferometer 850 includes: a light source 815, a detector 825, a mirror 835, a beamsplitter 845, and a moving stage or positioner 855 oil which mirror 835 is mounted.

Light source 815 may be a superluminescent diode (SLD) or other broad band source. Beneficially, light source 815 outputs light spanning or substantially spanning the visible spectrum (i.e., "white light").

Operationally, light source 815 generates light having a broad spectral bandwidth and provides the light to beamsplitter 845. Beamsplitter 845 divides the light into a first portion and a second portion. The first portion of the light is provided via optical fiber 830 and collimating lens 840 to illuminate object under test 805 and the reference surface of structure 810. At least some of this light is reflected and/or refracted by object 805 and the reference surface of structure 810 back through collimating lens 840 and optical fiber 830 to detector 825, via beamsplitter 845. Meanwhile, the second portion of the light from beamsplitter 845 is provided to illuminate mirror 835. Mirror 835 reflects at least some of the second portion of the light to detector 825 via beamsplitter 845.

Detector 825 is adapted to output a signal indicating when an optical path length traveled by the first portion of the light from beamsplitter 845 to detector 825 is the same as the optical path length traveled by the second portion of the light from beamsplitter 845 to detector 825. Fringe contrast will be obtained only when those distances traveled by light iii the two arms of the interferometer exactly match. By scanning mirror 835 in the reference arm, a signal will be obtained every time the reference arm distance matches the distance to the surface of object 805 from which light is being reflected/refracted.

Accordingly, an optical path length traveled by the second portion of the light from the beamsplitter, to mirror 835, and back through beamsplitter 845 to detector 825 is adjusted until detector 825 outputs a signal indicating a first interference fringe caused by light refracted or reflected by a first surface of object 805. In the embodiment of FIG. 8, the optical path length is adjusted by moving positioner 855 on which mirror 835 is mounted. However, other means for adjusting the optical path length are possible in place of positioner 855, including attaching mirror 835 to a piezo driver or voice coil actuator.

Then, the optical path length traveled by the second portion of the light is adjusted again until detector 825 outputs a signal indicating a second interference fringe caused by light refracted or reflected by a second surface of object 805.

Next, the optical path length traveled by the second portion of the light is adjusted yet again until detector 825 outputs a signal indicating a third interference fringe caused by light refracted or reflected by the reference surface of structure 810. The reference surface allows self-calibration of geometric measurement system 800 to assist in eliminating any errors in determining the optical path length traveled by the second portion of the light in the reference arm of the system when an interference fringe is produced from light reflected or refracted by a surface of object 805.

Since, as noted above, an interference fringe is only produced when the optical path lengths traveled by the first and second portions of the light are the same, it is possible to determine a distance to (and thereby the position of) a location on the surface of object 805 from which the light is reflected or refracted by determining the optical path length traveled by the second portion of the light reflected by mirror 835 when the detector 835 outputs the signal indicating the occurrence of an interference fringe. In one embodiment, this optical path length may be determined from a positional scale associated with positioner 855. Alternatively, a ramp signal, for example, may be used to drive a piezoelectric device or voice coil actuator to move mirror 835 along a linear path, and the times at which detector 825 outputs the signals indicating the interference fringes are measured to determine the distance to (and thereby the position of) the portion of a surface of object 805 from which light is being reflected/refracted.

While this method described measures only a single point of an object's surface at a time, it can do so at fairly high bandwidth (10 kHz). It is similar to light based radar in that a signal is obtained from each surface that the light encounters. Thus, there is no difficulty separating the signals from different surfaces.

With the addition of the goniometric scheme illustrated in FIGS. 4A-C and 5A-C, geometric measurement system 800 can be used to produce profiles of a contact lens' geometry including base curvature, front curvature and thickness. In addition, by rotating the contact lens, multiple meridians can also be measured and analyzed.

Geometric measurement systems as described above may be employed for measuring a variety of objects, including for example: molds, dry contact lenses in molds, contact lenses in a fixture, intraocular lenses (IOLs), IOL molds, lenses, aspheric lenses, plastic molds, mirrors, human or animal corneas, and other objects, particularly but not limited to objects having one or more highly curved, potentially aspheric and non-symmetric surfaces and/or one or more surfaces that passes a substantial amount of light (e.g., more than 10% of incident light, and more typically more than 50% of incident light) therethrough. Beneficially the system can be manually loaded, or automated. Also beneficially, the system will test the presented object, display the results, record the surface shape, and save the data to a data storage device (e.g., memory and/or a disk drive, etc.). Each measurement can be correlated to a part number and batch ID, and/or any other pertinent information, as it is delivered to the system.

Beneficially, system components are enclosed inside a housing providing a controlled environment inside the system work envelope. All of the stages and critical system components are mounted to a solid base capable of providing thermal and optical stability, thus insuring measurement accuracy.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

We claim:

1. A system for determining at least one geometric characteristic of an object having a first surface and a second surface, wherein at least one of the first and second surfaces passes a substantial amount of light therethrough, the system comprising:

a light source adapted to illuminate the object;

an optical element adapted to receive light from the first and second surfaces of the object and to produce a first light beam corresponding to light from the first surface of the object and a second light beam corresponding to light from the second surface of the object;

a light intensity detector having a radiation sensitive surface adapted to receive the first and second light beams and to detect the intensity of incident radiation on the radiation sensitive surface from the first and second light beams, and to produce an output that provides a measure of the intensity of the incident radiation;

a translator adapted to adjust relative positions of the optical element and the light intensity detector; and a processor adapted to determine wavefronts of the light from the first and second surfaces based on the output of the light intensity detector at a plurality of different relative positions.

2. The system of claim 1, where the processor is adapted to execute a phase retrieval algorithm to retrieve phase information based on the output of the light intensity detector.

3. A method of determining at least one geometric characteristic of an object having a first surface and a second surface, wherein at least one of the first and second surfaces passes a substantial amount of light therethrough, the method comprising:

(a) illuminating the object;

(b) transmitting light from the first and second surfaces of the object through an optical element to produce a first light beam corresponding to light from the first surface of the object and a second light beam corresponding to light from the second surface of the object;

(c) detecting the intensity of incident radiation on a radiation sensitive surface from the first and second light beams;

(d) adjusting relative positions of the optical element and the radiation sensitive surface, and at each of a plurality of different relative positions producing an output that provides a measure of the intensity of the incident radiation; and (e) determining wavefronts of the light from the first and second surfaces of the object based on the outputs produced at each of the different relative positions.

4. The method of claim 2, wherein determining wavefronts of the light from the first and second surfaces of the object includes executing a phase retrieval algorithm to retrieve phase information based on the output of the light intensity detector.

5. A system for determining at least one geometric characteristic of an object having a first surface and a second surface, wherein at least one of the first and second surfaces passes a substantial amount of light therethrough, the system comprising:

a light source adapted to illuminate the object;

a diffractive optical element adapted to receive light from the first and second surfaces of the object and to produce therefrom at least two spatially-separated light distributions having at least one statistical characteristic different from each other;

a light intensity detector having a radiation sensitive surface adapted to receive the at least two spatially-separated light distributions, to detect the at least two spatially-separated light distributions at different points across the radiation sensitive surface, and to produce an output that provides a measure of the intensity of the incident radiation at the different points; and a processor adapted to determine wavefronts of the light from the first and second surfaces based on the output of the light intensity detector.

6. The system of claim 5, where the diffractive optical element includes a lens.

7. The system of claim 5, where the diffractive optical element includes a diffraction grating with defocus fringes.

8. The system of claim 5, wherein the light intensity detector detects at least the positive and negative first orders of the diffracted light.

9. The system of claim 5, wherein the processor is adapted to determine a thickness variation of the object from the wavefronts of the light from the first and second surfaces.

10. The system of claim 5, wherein the at least one statistical characteristic includes at least one of defocus, coma, spherical aberration, and a higher order aberration.

11. The system of claim 5, wherein the light source is adapted to illuminate the entire first and second surfaces of the object.

12. The system of claim 5, further comprising a translator adapted to adjust relative positions of the light source and the object such that, at each relative position, the light from the light source is delivered onto a sub-region of each of the first and second surfaces such that adjacent sub-regions have an overlap portion, wherein the processor is adapted to stitch together wavefronts measured by the wavefront sensor for different sub-regions of each of the surfaces at relative positions provided by the translator, including using derivatives of wavefronts in overlap regions, to construct the wavefronts of the light from the first and second surfaces.

13. A method of determining at least one geometric characteristic of an object having a first surface and a second surface, at least one of the first and second surfaces passing a substantial amount of light therethrough, the method comprising:

(a) illuminating the object;

(b) transmitting light from the first and second surfaces of the object through a diffractive optical element to produce therefrom at least two spatially-separated light distributions having at least one statistical characteristic different from each other;

(c) detecting the intensity of incident radiation on a radiation sensitive surface from the at least two spatially-separated light distributions at different points on the radiation sensitive surface to produce an output that provides a measure of the intensity of the incident radiation at the different points;

(d) determining wavefronts of the light from the first and second surfaces of the object based on the output of the detection.

14. The method of claim 13, further comprising passing the diffracted light through a diffraction grating with defocus fringes.

15. The method of claim 13, wherein detecting the intensity of incident radiation on a radiation sensitive surface from the diffracted light at different points on the radiation sensitive surface includes detecting at least the positive and negative first orders of the diffracted light.

16. The method of claim 13, further comprising determining a thickness variation of the object from the wavefronts of the light from the first and second surfaces.

17. The method of claim 13, wherein illuminating the substantially optically transparent object includes illuminating the entire first and second surfaces of the object.

18. The method of claim 13, further comprising:

adjusting relative positions of a light source and the object such that, at each relative position, the light from the light source is delivered onto a sub-region of each of the first and second surfaces such that adjacent sub-regions have an overlap portion, wherein the processor is adapted to stitch together wavefronts measured by the wavefront sensor for different sub-regions of each of the surfaces at relative positions provided by the translator, including using derivatives of wavefronts in overlap regions, to construct the wavefronts of the light from the first and second surfaces.

* * * * *